United States Patent [19]

Charbonneau et al.

[11] Patent Number: 4,994,262
[45] Date of Patent: Feb. 19, 1991

[54] ORAL COMPOSITIONS

[75] Inventors: Duane L. Charbonneau, Middletown; Mark D. Evans; Lincoln D. Germain, both of Cincinnati; Martin S. Robin, Wyoming, all of Ohio

[73] Assignee: The Procter & Gamble Company, Cincinnati, Ohio

[21] Appl. No.: 356,962

[22] Filed: May 25, 1989

Related U.S. Application Data

[63] Continuation-in-part of Ser. No. 258,257, Oct. 14, 1988, abandoned.

[51] Int. Cl.$^5$ .............................................. A61K 9/18
[52] U.S. Cl. ....................................... 424/52; 424/57; 514/900; 514/902
[58] Field of Search .................... 424/449, 25, 55; 514/900, 902

[56] References Cited

U.S. PATENT DOCUMENTS

| 3,937,807 | 2/1976 | Haefele | 424/52 |
| 4,118,471 | 10/1978 | Pensak | 424/49 |
| 4,666,708 | 5/1987 | Goldemberg et al. | 424/49 |

FOREIGN PATENT DOCUMENTS

WO88/00463  1/1988  World Int. Prop. O. .

Primary Examiner—Shep K. Rose
Attorney, Agent, or Firm—Douglas C. Mohl; Kim W. Zerby; Jack D. Schaeffer

[57] ABSTRACT

Oral compositions containing a cationic antimicrobial agent and benzoic acid and phthalic acid or salts of these acids, which compositions are effective against plaque and gingivitis, are disclosed. Also disclosed are methods for reducing plaque and gingivitis.

15 Claims, No Drawings

ORAL COMPOSITIONS

CROSS REFERENCE TO RELATED APPLICATION

This is a continuation-in-part of application Ser. No. 258,257, filed on Oct. 14, 1988, now abandoned.

TECHNICAL FIELD

The present invention relates to oral compositions containing a cationic antimicrobial agent, benzoic acid and phthalic acid or salts thereof and a suitable vehicle, which compositions are effective against plaque/gingivitis.

BACKGROUND ART

Plaque is an organic mixture of living bacteria found in the mouth. The bacteria can secrete acids, enzymes and microtoxins which can cause caries and periodontal disease such as gingivitis.

The use of antimicrobial agents to reduce plaque/gingivitis as well as mouth odor has been recognized for many years. Included among references disclosing oral compositions containing antimicrobials are U.S. Pat. No. 3,937,805, Feb. 10, 1976 to Harrison; U.S. Pat. No. 3,937,807, Feb. 10, 1976 to Haefele; U.S. Pat. No. 4,080,441, Mar. 21, 1978 to Gaffar et al.; U.S. Pat. No. 4,118,474, Oct. 3, 1978 to Gaffar et al.; U.S. Pat. No. 4,241,049, Dec. 23, 1980 to Colodney et al.; U.S. Pat. No. 3,925,543, Dec. 9, 1975 to Donohue; and U.S. Pat. No. 4,256,731, Mar. 17, 1981 to Curtis et al.

Additionally, U.S. Pat. No. 4,666,708, May 19, 1987 to Goldemberg et al. discloses alkaline mouthwash compositions containing a benzoate salt and possibly a cationic antimicrobial. WO-88/00468, Jan. 28, 1988 discloses toothpaste compositions containing a benzoate salt and optionally a cationic biocide.

While the prior art discloses the use of antimicrobials and benzoate salts in oral products, there is still the need for additional formulations which will provide enhanced performance against plaque/gingivitis.

It has now been found that by using a mixture of phthalate and benzoate acids or salts with a cationic antimicrobial, antiplaque and antigingivitis activity is achieved.

It is still a further object of the present invention to provide a method for reducing plaque/gingivitis.

These and other objects will become more apparent from the detailed description which follows. All percentages and ratios herein are by weight and all measurements are made at 25° C. unless otherwise specified.

SUMMARY OF THE INVENTION

The present invention relates to mouthwash compositions which provide antiplaque/antigingivitis benefits comprising:
(a) a safe and effective amount of a cationic antimicrobial agent;
(b) a safe and effective amount of phthalate acid or a suitable water soluble salt thereof;
(c) a safe and effective amount of benzoic acid or a suitable water soluble salt thereof; and
(d) a suitable carrier.

Methods of reducing plaque and gingivitis are also disclosed.

DETAILED DESCRIPTION OF THE INVENTION

The compositions of this invention employ a cationic antimicrobial agent, a mixture of phthalic and benzoic acids or salts thereof and a suitable mouthwash carrier. These and other components will be described in detail hereinafter.

By "safe and effective amount" as used herein, means sufficient compound to reduce plaque/gingivitis and/or enhance such reduction while being safe to the hard and soft tissues of the oral cavity.

By the term "comprising", as used herein, is meant that various additional components can be conjointly employed in the compositions of this invention as long as the actives perform their intended functions.

By the term "carrier", as used herein, is meant a suitable vehicle which can be used to apply the active components to the oral cavity.

CATIONIC ANTIMICROBIAL

The antimicrobials used in the compositions of the present invention can be any of a wide variety of cationic antimicrobial agents such as quaternary ammonium compounds (e.g., cetyl pyridinium chloride), and substituted guanidines such as chlorhexidine and the corresponding compound alexidine. Mixtures of cationic antimicrobials may also be used in the present invention.

Antimicrobial quaternary ammonium compounds include those in which one or two of the substituents on the quaternary nitrogen has a carbon chain length (typically alkyl group) of some 8 to 20, typically 10 to 18 carbon atoms while the remaining substituents (typically alkyl or benzyl group) have a lower number of carbon atoms, such as 1 to 7 carbon atoms, typically methyl or ethyl groups. Dodecyl trimethyl ammonium bromide, tetradecyl pyridinium chloride, domiphen bromide, tetradecyl ethyl pyridinium chloride, dodecyl dimethyl(2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride and benzethonium chloride are exemplary of typical quaternary ammonium antibacterial agents. Other compounds are the bis[4-(R-amino)-1-pyridinium] alkanes as disclosed in U.S. Pat. No. 4,206,215, June 3, 1980 to Bailey incorporated herein by reference. The pyridinium compounds are the preferred quaternary ammonium compounds for mouthwash executions while the benzalkonium chloride and benzethonium chloride are preferred for dentifrice use.

The substituted guanidines of this invention include bisbiguanide compounds having the generic formula:

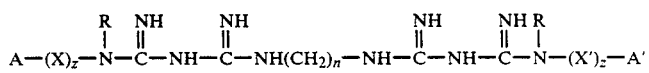

wherein A and A' each represent either (1) a phenyl radical which optionally is substituted by an alkyl or alkoxy group containing from 1 to about 4 carbon atoms, a nitro group, or a halogen atom; (2) an alkyl group containing from about 1 to about 12 carbon atoms; or (3) alicyclic groups containing from 4 to about 12 carbon atoms; wherein X and X' each represent an alkylene radical containing from 1 to 3 carbon atoms; wherein Z and Z' each can be either 0 or 1; wherein R and R' each represent either hydrogen, an alkyl radical containing from 1 to about 12 carbon atoms, or an aralkyl radical containing from 7 to about 12 carbon atoms; wherein n is an integer from 2 to 12 inclusive; wherein the polymethylene chain$(CH_2)_n$ may optionally be interrupted by oxygen or sulfur atoms, aromatic nuclei, etc. The water soluble salts of the above compounds are preferred for use herein. Suitable water soluble salts include the chloride, the fluoride, and especially the acetate salt. The preferred substituted guanidine is chlorhexidine-[1,6-di(-$N^5$-pchlorophenyl-N-diguanido)-hexane].

The cationic antimicrobial is generally used in the present compositions at a level of from about 0.02% to about 1%, preferably from about 0.02% to about 0.5%, most preferably from about 0.04% to about 0.3%.

Benzoic and Phthalic Acids and Water Soluble Salts Thereof

Also included in the present compositions are benzoic acid and phthalic acid or their water soluble salts. The counterions useful in these salts are generally alkali metal and ammonium ions. The preferred benzoate salt is sodium benzoate while the preferred phthalate salt is potassium biphthalate.

In the present compositions the benzoic acid or a benzoate salt is present generally at a level of from about 0.01% to about 3%, preferably from about 0.1% to about 2%. The phthalic acid or phthalate salt is present at a level of from about 0.01% to about 5%, preferably from about 0.1% to about 3%.

Carriers

Conventional mouthwash composition components can comprise the carrier for the antimicrobial and salts of the present invention. Mouthwashes generally comprise about 20:1 to about 2:1 of a water/ethyl alcohol solution and preferably other ingredients such as flavor, sweeteners, humectants and surfactants. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Suitable humectants include sorbitol and glycerin while suitable surfactants include oleate and laurate esters of sorbitol and its anhydride condensed with ethylene oxide as well as ethylene oxide and propylene oxide condensates.

Other types of surfactants which may be used include amphoterics. The amphoteric sudsing agents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water-solubilizing group, e.g., carboxylate, sulfonate, sulfate, phosphate, or phosphonate.

Generally, on a weight basis the mouthwashes of the invention comprise 5% to 30% (preferably 5% to 20%) ethyl alcohol, 0% to 25% (preferably 3% to 20%) of a humectant, 0% to 5% (preferably 0.01% to 0.5%) surfactant, 0% to 0.5% (preferably 0.005% to 0.06%) sweetening agent, 0% to 0.3% (preferably 0.03% to 0.3%) flavoring agent, and the balance water.

Toothpastes and toothpowders are also suitable carriers and contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein. Of course the abrasive selected should also exhibit excellent compatibility with soluble cationic therapeutic sources.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent". These silica abrasive are described in U.S. Pat. No. 4,340,583, July 29, 1982, incorporated herein by reference.

The abrasive in the dentifrice compositions described herein is present at a level of from about 6% to about 70%, preferably from about 15% to about 25% when the dentifrice is a toothpaste. Higher levels, as high as 90%, may be used if the composition is a toothpowder.

Flavoring agents can also be added to the dentifrice and other compositions of the present invention. Suitable flavoring agents include oil of wintergreen, oil of peppermint, oil of spearmint, oil of sassafras, and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

The dentifrice compositions of this invention may also contain emulsifying agents. Suitable emulsifying agents are those which are reasonably stable and foam throughout a wide pH range, including non-soap anionic, nonionic, cationic, zwitterionic and amphoteric organic synthetic detergents. Nonionic surfactants are preferred. Many of these suitable surfactants are disclosed by Gieske et al. in U.S. Pat. No. 4,051,234, Sept. 27, 1977 incorporated herein by reference.

Water is also present in the toothpaste compositions of this invention. Water employed in the preparation of commercially suitable compositions should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth and polysaccharide gums such as xanthan gum can also be used. Colloidal magnesium aluminum silicate or finely divided silica can be used as part of the thickening agent to further improve texture. Hydroxyethyl cellulose is a preferred binder. Thickening agents in an amount from 0.5% to 5.0% by weight of the total composition may be used.

It is also desirable to include a humectant in a toothpaste to keep it from hardening. Suitable humectants include glycerin, sorbitol, and other edible polyhydric alcohols at a level of from about 10% to about 70%.

Other vehicles include lozenges and chewing gums. Components useful in such compositions are disclosed in U.S. Pat. No. 4,083,955, Apr. 11, 1978 to Grabenstetter et al., incorporated herein by reference.

Another suitable vehicle is a topical gel. Suitable topical dental gels generally comprise a base of a humectant such as glycerine thickened with a suitable agent. Such gels generally do not contain an abrasive.

An optional ingredient which may be useful in any of the present compositions is an antistain agent. As with other antimicrobials the cationic antimicrobial materials used in the present compositions may cause staining when used at fairly high levels. Antistain agents include carboxylic acids such as those disclosed in U.S. Pat. No. 4,256,731, May 17, 1981 to Curtis et al., incorporated herein by reference. Other agents include amino carboxylate compounds as disclosed in U.S. Pat. No. 3,937,807, Feb. 10, 1976 to Haefele; dicarboxylic acid esters as disclosed in U.S. Pat. No. 4,080,441, Mar. 21, 1978 to to Gaffar et al.; and phosphonoacetic acid as disclosed in U.S. Pat. No. 4,118,474, Oct. 3, 1978 to Gaffar et al. All of these patents are also incorporated herein by reference.

Another useful optional component is a soluble fluoride ion source. The number of such sources is great and includes, among others, those disclosed in U.S. Pat. No. 3,535,421, Oct. 20, 1970 to Briner et al. incorporated herein by reference. Typical sources include stannous fluoride, potassium fluoride, indium fluoride, sodium fluoride, sodium monofluorophosphate, alanine hydrofluoride as well as many others. The preferred source is sodium fluoride used at a level sufficient to provide from about 25 ppm $F^-$ to about 250 ppm for a rinse and about 1100 ppm for a toothpaste.

Another useful agent for incorporation into the present compositions is a soluble pyrophosphate salt such as di and tetra alkali metal pyrophosphate salts. These salts are generally used in amounts sufficient to provide at least about 1% $P_2O_7$ and are described in U.S. Pat. No. 4,515,772, May 7, 1985 to Parran et al. incorporated herein by reference.

Many other agents in addition to those discussed herein may also be used. If used the agents are generally in an amount of 0.05% or greater. The antistain active may be used in the same composition with the cationic compound or in a separate composition used sequentially with the cationic compound.

The pH of the present compositions and/or its pH in the mouth can be any pH which is safe for the mouth's hard and soft tissues. Such pH's are generally from about 3 to about 10, preferably from about 4 to about 8.

METHOD OF MANUFACTURE

The carrier compositions of the present invention can be made using methods which are common in the oral products area.

COMPOSITION USE

The present invention in its method aspect involves applying to the oral cavity safe and effective amounts of the antimicrobial. Generally an amount of at least about 0.001 g of the antimicrobial is effective.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLE I

The following is a mouthwash representative of the present invention:

| Component | Weight % |
|---|---|
| Ethyl Alcohol | 6.500 |
| PEG 40 SDIS | 0.100 |
| Flavor | 0.120 |
| Ethylene Glycol/Propylene Glycol Condensate Nonionic Surfactant | 0.150 |
| Double reverse osmosis water | 84.200 |
| Sodium Benzoate | 0.600 |
| Monosodium phosphate | 0.500 |
| Benzoic Acid | 0.020 |
| Potassium Biphthalate | 2.000 |
| Cetyl Pyridinium Chloride | 0.100 |
| Glycerin | 5.000 |
| Sodium Fluoride | 0.020 |
| Sodium Saccharin | 0.020 |
| Dye (1% Solution) | 0.070 |
| Sodium Hydroxide (50% solution) | 0.600 (q.s. to pH) |
| Total | 100.000 |

EXAMPLE II

The following is another mouthwash representative of the present invention:

| Component | Weight % |
|---|---|
| Ethyl Alcohol | 15.000 |
| PEG 40 SDIS | 0.500 |
| Flavor | 0.200 |
| Double reverse osmosis water | 71.560 |
| Sodium Benzoate | 0.200 |
| Monosodium phosphate | 1.000 |
| Benzoic Acid | 0.020 |
| Potassium Biphthalate | 1.000 |
| Cetyl Pyridinium Chloride | 0.050 |
| Glycerin | 10.00 |
| Sodium Fluoride | 0.050 |
| Sodium Saccharin | 0.020 |
| Dye (1% Solution) | 0.100 |
| Sodium Hydroxide (50% Solution) | 0.300 (q.s. to pH) |
| Total | 100.000 |

EXAMPLE III

The following is another mouthwash representative of the present invention:

| Component | Weight % |
| --- | --- |
| Ethyl Alcohol | 10.000 |
| Ethylene Glycol/Propylene Glycol Condensate Nonionic Surfactant | 0.150 |
| Flavor | 0.160 |
| PEG 40 SDIS | 0.160 |
| Double reverse osmosis water | 82.230 |
| Sodium Benzoate | 0.500 |
| Monosodium phosphate | 0.700 |
| Benzoic Acid | 0.020 |
| Potassium Biphthalate | 0.615 |
| Cetyl Pyridinium Chloride | 0.075 |
| Glycerin | 5.000 |
| Sodium Fluoride | 0.050 |
| Sodium Saccharin | 0.060 |
| Dye (1% Solution) | 0.070 |
| Sodium Hydroxide (50% Solution) | 0.210 (q.s. to pH) |
| Total | 100.00 |

EXAMPLE IV

The following is a toothpaste composition representative of the present invention:

| Component | Weight % |
| --- | --- |
| Double Reverse Osmosis Water | 14.300 |
| Sorbitol (70%) | 42.525 |
| Sodium Fluoride | 0.243 |
| Sodium Saccharin | 0.460 |
| Benzethonium Chloride (98.8%) | 1.012 |
| Sodium Benzoate | 1.000 |
| Potassium Biphthalate | 3.000 |
| NaOH (50%) | 1.400 |
| PEG-6 | 3.000 |
| Titanium dioxide | 0.500 |
| Dye (1% solution) | 0.050 |
| Silica | 22.000 |
| Glycerin | 7.000 |
| Hydroxyethyl Cellulose | 1.250 |
| Flavor | 1.100 |
| PEG 40 SDIS | 1.160 |
| Total | 100.000 |

EXAMPLES V-VII

Given below are additional toothpaste compositions of the present invention:

| Component | Weight % V | Weight % VI | Weight % VII |
| --- | --- | --- | --- |
| Double Reverse Osmosis Water | 14.300 | 14.300 | 14.300 |
| Silica | 22.000 | 22.000 | 22.000 |
| Sorbitol (70%) | 42.079 | 42.085 | 42.525 |
| Glycerine | 7.000 | 7.000 | 7.000 |
| Sodium Fluoride | 0.243 | 0.243 | 0.243 |
| Benzethonium Chloride (98.8%) | 0.506 | — | 1.012 |
| Domiphen Bromide | — | 0.500 | — |
| Sodium Benzoate | 1.000 | 1.000 | 1.000 |
| Phthalic Acid | 2.427 | 2.427 | — |
| Potassium Biphthalate | — | — | 3.000 |
| Sodium Hydroxide (50%) | 2.435 | 2.435 | 1.400 |
| PEG-6 | 3.000 | 3.000 | 3.000 |
| Titanium Dioxide | 0.500 | 0.500 | 0.500 |
| Flavor | 1.000 | 1.000 | 1.100 |
| Sweetener | 0.850 | 0.850 | 0.460 |
| PEG-40 SDIS | 1.160 | 1.160 | 1.160 |
| Hydroxyethylcellulose | 1.500 | 1.500 | 1.250 |
| Dye | — | — | 0.050 |
|  | 100.000 | 100.000 | 100.000 |

The above compositions are useful in reducing the incidence of plaque and gingivitis. Other vehicles such as lozenges, chewing gums and dental gels may also be used to deliver the actives. Other cationic actives such as substituted biquanides, dodecyl trimethyl ammonium bromide, tetradecyl pyridinium chloride, domiphen bromide, tetradecyl ethyl pyridinium chloride, dodecyl dimethyl(2-phenoxyethyl) ammonium bromide, benzyl dimethylstearyl ammonium chloride, quaternized 5-amino-1,3-bis(2-ethyl-hexyl)-5-methyl hexa hydropyrimidine and benzalkonium chloride may be used.

What is claimed is:

1. An oral mouthwash or toothpaste composition comprising:
   (a) from about 0.02% to about 1.5% of a cationic antimicrobial;
   (b) from about 0.01% to about 3% of a benzoate salt;
   (c) from about 0.01% to about 5% of a phthalate salt; and
   (d) a mouthwash or toothpaste carrier.

2. A mouthwash composition according to claim 1 wherein the cationic antimicrobial is cetyl pyridinium chloride.

3. A mouthwash composition according to claim 2 wherein the benzoate salt is a sodium salt and the phthalate salt is a potassium salt.

4. A mouthwash composition according to claim 3 which contains a humectant.

5. A mouthwash composition according to claim 4 which contains a nonionic surfactant.

6. A mouthwash composition according to claim 5 wherein the humectant is glycerin or sorbitol.

7. A mouthwash composition according to claim 2 which in addition contains a soluble fluoride ion source.

8. A mouthwash composition according to claim 2 which in addition contains a soluble pyrophosphate salt.

9. A toothpaste composition according to claim 1 wherein the benzoate salt is present at a level of from about 0.01% to about 3% and the phthalate salt is present at a level of from about 0.01% to about 5%.

10. A toothpaste composition according to claim 9 wherein the cationic antimicrobial is benzalkonium chloride.

11. A toothpaste composition according to claim 10 wherein the benzoate salt is a sodium salt and the phthalate salt is a potassium salt.

12. A toothpaste composition according to claim 11 which in addition contains a humectant.

13. A toothpaste composition according to claim 12 which in addition contains a nonionic surfactant.

14. A toothpaste composition according to claim 9 which in addition contains a soluble fluoride ion source.

15. A toothpaste composition according to claim 9 which in addition contains a soluble pyrophosphate salt.

* * * * *